United States Patent [19]

Schroeder

[11] Patent Number: 5,354,898
[45] Date of Patent: Oct. 11, 1994

[54] METHOD FOR PURIFYING CRUDE AROMATIC CARBOXYLIC ACIDS

[75] Inventor: Hobe Schroeder, Naperville, Ill.

[73] Assignee: Amoco Corporation, Chicago, Ill.

[21] Appl. No.: 78,623

[22] Filed: Jun. 17, 1993

[51] Int. Cl.⁵ .......................................... C07C 51/42
[52] U.S. Cl. .................................. 562/485; 562/487
[58] Field of Search ...................... 562/485, 487, 485; 554/194

[56] References Cited

U.S. PATENT DOCUMENTS

| | | | |
|---|---|---|---|
| 3,584,039 | 6/1971 | Meyer et al. | 260/525 |
| 3,726,915 | 4/1973 | Pohlmann | 260/525 |
| 4,311,738 | 1/1982 | Chi | 427/387 |
| 4,629,715 | 12/1986 | Schroeder | 502/185 |
| 4,743,577 | 5/1988 | Schroeder et al. | 502/326 |
| 4,831,008 | 5/1989 | Timmer et al. | 502/328 |
| 4,892,972 | 1/1990 | Schroeder et al. | 562/487 |
| 5,051,308 | 9/1991 | Reed et al. | 428/412 |

OTHER PUBLICATIONS

M. Bankmann et al., "Forming of High Surface Area TiO₂ to Catalyst Supports," Symposium on Catalyst Supports: Chemistry, Forming and Characterization, presented before the Division of Petroleum Chemistry, Inc., American Chemical Society, New York City Meeting, Aug. 25–30, 1991.

M. Bankmann et al., "Forming of High Surface Area TiO₂ to Catalyst Supports," *Catalysis Today*, vol. 14, pp. 225–242 (1992).

Sikkenga et al., pending U.S. patent application Ser. No. 07/900,593, filed Jun. 8, 1992, in particular, p. 11, lines 23–31.

Holzhauer et al., pending U.S. patent application Ser. No. 07/900,637, filed Jun. 18, 1992, in particular, p. 27, lines 1–12.

Schroeder et al., pending U.S. patent application Ser. No. 08/029,037, filed Mar. 10, 1993.

*Primary Examiner*—Jose G. Dees
*Assistant Examiner*—Samuel Barts
*Attorney, Agent, or Firm*—Thomas E. Nemo; Wallace L. Oliver

[57] ABSTRACT

A method is disclosed for the purification of crude aromatic carboxylic acid by passing a solution of crude aromatic carboxylic acid in the presence of hydrogen through a first zone containing a hydrogenation catalyst based on a carbon carrier material then passing the solution through an abrasion resistant material thereby reducing the amount of carbon particles contained in the purified aromatic carboxylic acid.

11 Claims, 1 Drawing Sheet

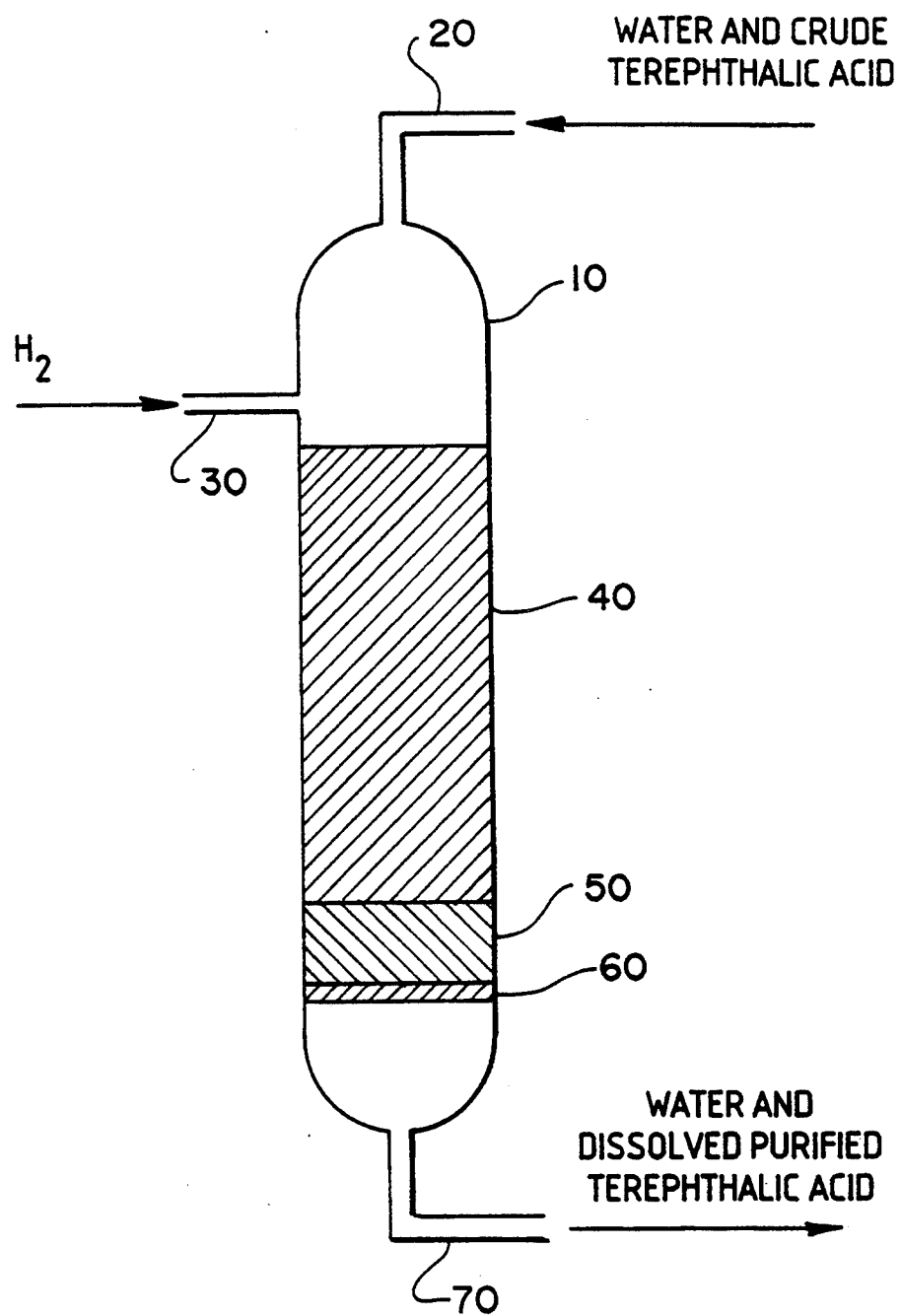

METHOD FOR PURIFYING CRUDE AROMATIC CARBOXYLIC ACIDS

BACKGROUND OF THE INVENTION

1. Field of the Invention

This invention relates generally to a method for preparing purified aromatic carboxylic acids and a means for effecting such purification. More particularly, this invention relates to a method for preparing purified aromatic carboxylic acids such as purified terephthalic acid, purified isophthalic acid and purified naphthalenedicarboxylic acid wherein the purified aromatic carboxylic has a reduced level of particulate contaminates.

2. Discussion of the Prior Art

Polymer grade aromatic carboxylic acids such as "purified" terephthalic acid or isophthalic acid are the starting materials for polyethylene terephthalates and isophthalates, respectively, which are the principal polymers employed in the manufacture of polyester fibers, polyester films, and resins for bottles and like containers. Similarly, polymer grade or "purified" naphthalene dicarboxylic acids, especially 2,6-naphthalene dicarboxylic acid, are the starting materials for polyethylene naphthalates, which can also be employed in the manufacture of fibers, films and resins. A purified terephthalic acid, isophthalic acid or naphthalene dicarboxylic acid can be derived from a relatively less pure, technical grade or "crude" terephthalic acid, isophthalic acid or "crude" naphthalene dicarboxylic acid, respectively, by purification of the crude acid utilizing hydrogen and a noble metal catalyst, as described for terephthalic acid in U.S. Pat. No. 3,584,039 to Meyer. In the purification process, the impure terephthalic acid, isophthalic acid or naphthalene dicarboxylic acid is dissolved in water or other suitable solvent or solvent mixture at an elevated temperature, and the resulting solution is hydrogenated, preferably in the presence of a hydrogenation catalyst, which conventionally is palladium on a carbon support, as described in Pohlmann, U.S. Pat. No. 3,726,915. This hydrogenation step converts the various color bodies present in the relatively impure phthalic acid or naphthalene dicarboxylic acid to colorless products. Another related purification-by-hydrogenation process for aromatic polycarboxylic acids produced by liquid phase catalyst oxidation of polyalkyl aromatic hydrocarbons is described in Stech et al., U.S. Pat. No. 4,405,809.

Carbon is conventionally used as the support material for the noble metal in the catalyst employed in the aforesaid purification method. A common disadvantage of the use of a carbon support is that carbon fines are often generated during commercial operations. The generation of such fines can be minimized but generally cannot be completely avoided. During the subsequent polymerization process to make polyester materials, such particulates introduced with the particular purified acid, for example, terephthalic acid, isophthalic acid or 2,6-naphthalene dicarboxylic acid, can plug filters and thereby cause interruptions in the process. Other such particulates that bypass the filter may be incorporated into the resulting polyester fiber or film and cause fiber breakage or film distortion.

In a typical reactor use to purify aromatic carboxylic acids, screens or other retaining means are employed for retaining the catalyst in the reactor vessel yet providing for the passage of the liquid reaction mixture containing the dissolved aromatic carboxylic acid being purified. Most of these purification reactors are arranged in a vertical fashion with the feed stream comprising aromatic carboxylic acid and solvent entering an upper part of the reactor. This solution passes through the reactor catalyst bed and exits at the bottom of the reactor. In this configuration, the catalyst particles are forced against the screen or other retaining means. Even if used in a horizontal position or where the flow is upward in a vertically arranged reactor, the flow of the reaction mixture through the reactor forces the catalyst bed against the retaining screen. The hard screens pressing against the soft carbon catalyst, which are usually irregularly shaped, cause an abrasion or attrition of the catalyst particles, and the fine carbon particles that break lose from the catalyst particles readily pass through the screen or other retaining means and contaminate the purified aromatic carboxylic acid. While it is possible to use catalyst support formulations that are more resistant to attrition, such as the catalysts described in U.S. patent application Ser. No. 08/029,037, filed on Mar. 10, 1993, it would be desirable to continue to use the catalyst based on carbon supports and having one or more hydrogenation catalyst compounds, such as Group VIII catalyst metals, deposited thereon. Because of the highly corrosive conditions under which the aforesaid purification is performed, it has proven difficult to develop suitable noncarbon catalyst supports for use in the purification catalyst. Thus, it would be highly desirable to have a method for the purification of aromatic carboxylic acid that utilizes carbon carrier materials for the noble metal catalyst yet does not introduce as much carbon particles in the purified aromatic carboxylic acid. The present invention provides such a method for the preparation of purified aromatic carboxylic acids such as purified terephthalic acid, purified isophthalic acid and purified naphthalenedicarboxylic acid, as well as a means for effecting such purification.

M. Bankmann, R. Brand, B. H. Engler and J. Ohmer, "Forming of High Surface Area $TiO_2$ to Catalyst Supports," Catalysis Today, Vol. 14, pages 225–242 (1992), contains an extensive discussion of the use of titanium dioxide having a high surface area as a catalyst support.

Schroeder et al., U.S. Pat. No. 4,743,577, discloses that the use of catalysts containing palladium finely dispersed on carbon in the aforesaid purification of terephthalic acid derived from the oxidation of p-xylene results in contamination of the resulting purified terephthalic acid with fines produced by abrasion of the carbon granulates due to their relatively low crush strength and poor abrasion resistance. This patent discloses that reduced fines contamination results from the use instead of a catalyst containing a thin layer of palladium, nickel, rhodium, platinum, copper, rhuthenium and cobalt on a porous sintered support of metallic titanium, zirconium, tungsten, chromium, nickel and alloys incorporating one or more of these metals. The surface area of palladium-plated supports of titanium, inconel and nickel are disclosed as 0.22, 0.55 and 1.21 square meters per gram, respectively, which are very significantly smaller than specific surface area of a palladium on active carbon catalyst.

Schroeder et al., U.S. Pat. No. 4,629,715, discloses that aqueous solution of crude terephthalic acid can be purified to relatively low 4-carboxy-benzaldehyde levels under hydrogenation conditions by using a layered catalyst bed wherein the first layer is constituted by palladium supported on an active carbon carrier and the second layer is constituted by rhodium supported on an active carbon carrier.

Schroeder et al., U.S. Pat. No. 4,892,972, discloses a method for the purification of a crude terephthalic acid by passing on aqueous solution of crude terephthalic acid in the presence of hydrogen through a first catalyst layer containing a Group VIII metal supported on a carbon carder wherein the Group VIII metal has a single electron in its outermost orbital in the ground state, and a second layer containing palladium supported on an active carbon carrier.

Sikkenga et al., pending U.S. patent application Ser. No. 07/900,593, filed Jun. 18, 1992, discloses the preparation of an aromatic carboxylic acid by the liquid phase catalyzed oxidation of an alkyl-substituted aromatic compound such as o-, m-, or p-xylene or 2,6-dimethyl-naphthalene. The application further discloses on page 11, lines 23-31, that the resulting aromatic carboxylic acids can be purified by hydrogenation thereof in the presence of a catalyst comprising one or more Group VIII metals deposited on a support such as alumina, titania or carbon.

Holzhauer et al., pending U.S. patent application Ser. No. 07/900,637, filed Jun. 18, 1992, discloses on page 27, lines 1-12, a method for purifying 2,6-naphthalene dicarboxylic acid by treating it with hydrogen in the presence of a hydrogenation catalyst containing one or more of platinum, palladium, rhodium, ruthenium, osmium and iridium supported on alumina, silica-alumina, silica, titania, clays and zirconia.

SUMMARY OF THE INVENTION

A method for purifying an aromatic carboxylic acid comprising passing a mixture of purification solvent and aromatic carboxylic acid, at a temperature of about 100° C. to about 350° C. and a pressure sufficient to maintain the purification solvent substantially in the liquid phase, through a first zone in a reactor vessel in the presence of hydrogen gas, the first zone having a catalyst comprising a carbon carrier material and at least one hydrogenation component, and subsequently passing the mixture through a second zone comprising abrasion resistant material, the second zone being positioned within the reactor vessel so that it is directly adjacent to a means for retaining catalyst within the reactor vessel, the catalyst retaining means being such that it will retain unabraded catalyst support material within the reactor vessel and also permit the passage of the mixture of purification solvent and aromatic carboxylic acid.

BRIEF DESCRIPTION OF THE DRAWING

FIG. 1 shows a mode of operating the method of this invention using one catalyst bed and one bed of abrasion resistant material.

DETAILED DESCRIPTION OF THE PREFERRED EMBODIMENTS

The method of this invention is suitable for use in the purification of an aromatic carboxylic acid such as crude terephthalic acid, isophthalic acid or a crude naphthalene dicarboxylic acid suitably prepared by the catalytic, liquid-phase oxidation of benzene having two oxidizable alkyl or acyl ring substituents or an oxidizable alkyl and acyl ring substituent in the meta or para positions or naphthalene having two oxidizable alkyl or acyl ring substituents or an oxidizable alkyl and acyl ring substituent in a solvent. Suitable alkyl groups contain from 1 to 6 carbon atoms, and suitable acyls also contain from 1 to 6 carbon atoms. Examples of suitable naphthalene-based aromatic feed compounds include: 1,2-dimethylnaphthalene, 2,6-dialkylnaphthalene or 2-acyl-6-alkylnaphthalene, 2,6-dimethyl-, 2,6-diethyl- or 2,6-diisopropyl-, 2-acetyl-6-methyl- and 2-methyl-6-ethylnaphthalene. The crude acid being purified preferably is either terephthalic acid formed by the oxidation of p-xylene, isophthalic acid formed by the oxidation of m-xylene or 2,6-naphthalene dicarboxylic acid formed by the oxidation of 2,6-dialkylnaphthalene (preferably 2,6-dimethylnaphthalene), and more preferably is terephthalic acid formed by the oxidation of p-xylene. It is of course understood that, prior to being purified, the crude acid, for example, 2,6-naphthalene dicarboxylic acid, can have been previously esterified to form the ester, for example, dimethyl naphthalene dicarboxylate, and then hydrolyzed to form the acid which is then purified by the method of this invention.

Suitable solvents for use in the oxidation step of the method for producing the crude acid that can be purified by the method of this invention include water and any aliphatic $C_2$-$C_6$ monocarboxylic acid such as acetic acid, propionic acid, n-butyric acid, isobutyric acid, n-valeric acid, trimethylacetic acid and caproic acid, and mixtures thereof. Preferably, the solvent is a mixture of acetic acid and water, which more preferably contains from 1 to 20 weight percent of water, as introduced into the oxidation reactor. Since heat generated in the highly exothermic liquid-phase oxidation is dissipated at least partially by vaporization of solvent in the oxidation reactor, some of the solvent is withdrawn from the reactor as a vapor, which is then condensed and recycled to the reactor. In addition, some solvent is withdrawn from the reactor as a liquid in the product stream. After separation of the crude acid product from the product stream, at least a portion of the mother liquor (solvent) in the resulting product stream is generally recycled to the reactor.

The source of molecular oxygen employed in the oxidation reaction for the aforesaid method for producing, for example, the crude phthalic acid or crude naphthalene dicarboxylic acid product that can be purified by the method of this invention can vary in molecular oxygen content from that of air to oxygen gas. Air is the preferred source of molecular oxygen. In order to avoid the formation of explosive mixtures, the oxygen-containing gas fed to the reactor should provide an exhaust gas-vapor mixture containing from 0.5 to 8 volume percent oxygen (measured on a solvent-free basis). For example, a feed rate of the oxygen-containing gas sufficient to provide oxygen in the amount of from 1.5 to 2.8 moles per methyl substituent of the m- or p-xylene or dimethylnaphthalene being oxidized will provide such 0.5 to 8 volume percent of oxygen (measured on a solvent-free basis) in the gas-vapor mixture in the condenser.

The catalyst employed in the aforesaid oxidation method for producing the crude aromatic acid, such as crude terephthalic or isophthalic acid or crude naphthalene dicarboxylic acid, comprises a heavy metal component, and can additionally comprise promoters or accelerators known in the art. In general, suitable heavy metal oxidation catalysts include those metals having an atomic number of about 21 to about 82, inclusive. A promoter such as a suitable source of bromide, a low molecular weight ketone having from 2 to 6 carbon atoms or a low molecular weight aldehyde having 1 to 6 carbon atoms can be used. The catalyst preferably comprises cobalt, more preferably comprises cobalt, and manganese-containing components, and most preferably comprises cobalt, manganese, and bromine-containing components. For example, the weight ratio of cobalt (calculated as elemental cobalt) in the cobalt component of the catalyst-to- p- or m-xylene, or -to-dialkyl, -diacyl or -acylalkylnaphthalene in the liquid-phase oxidation is in the range of from about 0.2 to about 30 milligram atoms (mga) per gram mole of the m- or p-xylene or dialkyl naphthalene. The weight ratio of manganese (calculated as elemental manganese) in the manganese component of the catalyst-to-cobalt (calculated as elemental cobalt) in the cobalt component of the catalyst in the liquid-phase oxidation is in the range of from about 0.2 to about 30 mga per mga of cobalt. The weight ratio of bromine (calculated as elemental bromine) in the bromine component of the catalyst-to-total cobalt and manganese (calculated as elemental cobalt and elemental manganese) in the cobalt and manganese components of the catalyst in the liquid-phase oxidation is in the range of from about 0.2 to about 1.5 mga per mga of total cobalt and manganese.

Each of the cobalt and manganese components can be provided in any of its known ionic or combined forms that provide reactive forms of cobalt, manganese, and bromine in the solvent in the reactor. For example, when the solvent is an acetic acid medium, cobalt and/or manganese carbonate, acetate tetrahydrate, and/or bromine can be employed. The 0.2:1.0 to 1.5:1.0 bromine-to-total cobalt and manganese milligram atom ratio is provided by a suitable source of bromine. Such bromine sources include elemental bromine ($Br_2$), or ionic bromide (for example, HBr, NaBr, KBr, $NH_4Br$, etc.), or organic bromides which are known to provide bromide ions at the operating temperature of the oxidation (e.g., bromobenzenes, benzylbromide, mono- and dibromoacetic acid, bromoacetyl bromide, tetrabromoethane, ethylenedibromide, etc.). The total bromine in molecular bromine and ionic bromide is used to determine satisfaction of the elemental bromine-to-total cobalt and manganese milligram atom ratio of 0.2:1.0 to 1.5:1.0. The bromine ion released from the organic bromides at the oxidation operating conditions can be readily determined by known analytical means. Tetrabromoethane, for example, at operating temperatures of 170° to 225° C. has been found to yield about 3 effective gram atoms of bromine per gram mole.

In operation, the minimum pressure at which the oxidation reactor is maintained is that pressure which will maintain a substantial liquid phase of the aromatic such as m- or p-xylene and at least 70 percent of the solvent. The m- or p-xylene or dialkylnaphthalene or other aromatic compound and solvent not in the liquid phase because of vaporization is removed from the oxidation reactor as a vapor-gas mixture, condensed, and then returned to the oxidation reactor. When the solvent is an acetic acid-water mixture, suitable reaction gauge pressures in the oxidation reactor are in the range of from about 0 $kg/cm^2$ to about 35 $kg/cm^2$, and typically are in the range of from about 10 $kg/cm^2$ to about 30 $kg/cm^2$. The temperature range within the oxidation reactor is generally from about 120° C., preferably from about 150° C., to about 240° C., preferably to about 230° C. The solvent residence time in the oxidation reactor is generally from about 20 to about 150 minutes and preferably from about 30 to about 120 minutes.

The oxidation can be performed either in a batch, continuous, or semicontinuous mode. In the batch mode, the aforesaid substituted aromatic to be oxidized, solvent and the catalyst components are initially introduced batchwise into the reactor, and the temperature and pressure of the reactor contents are then raised to the desired levels for the commencement of the oxidation reaction. Air is introduced continuously into the reactor. After commencement of the oxidation reaction, for example, after all of the aforesaid substituted benzene or naphthalene to be oxidized has been completely introduced into the reactor, the temperature of the reactor contents is raised. In the continuous mode, each of the aforesaid substituted aromatic compounds to be oxidized, air, solvent, and catalyst are continuously introduced into the oxidation reactor, and a product stream comprising the resulting crude acid oxidation product and catalyst components dissolved in the solvent is withdrawn from the reactor. In the semicontinuous mode, the solvent and catalyst are initially introduced into the reactor and then the aforesaid substituted aromatic compound to be oxidized and air are continuously introduced into the reactor.

For large-scale commercial operation, it is preferable to use a continuous oxidation process. In such a process, the weight ratio of monocarboxylic acid solvent to the aromatic feed to be oxidized is preferably about 2:1 to about 12:1, the mga ratio of manganese to cobalt is about 15:1 to about 0.3:1, the mga ratio of bromine to the total of cobalt and manganese is about 0.3:1 to about 0.8:1, and the total of cobalt and manganese, calculated as elemental cobalt and elemental manganese is at least about 0.40 weight percent based on the weight of the solvent, and the oxidation reaction temperature is about 185° C. to about 250° C. Acetic acid is the most suitable solvent for such preferred continuous oxidation.

Depending on the oxidation reaction conditions used, the aromatic feed compound selected, the oxidation catalysts, and the levels of catalyst selected, the reaction mixture produced in the oxidation reaction contains, in addition to the desired aromatic carboxylic acid, a number of impurities and reaction by-products. For example, terephthalic acid impurities are of several types. The compound 4-carboxybenzaldehyde (4-CBA), an intermediate product in the oxidation of para-xylene, is found in impure terephthalic acid. Unidentified color-forming precursors and color bodies, possibly of the fluorenone or anthraquinone structure, are also usually present. Nitro-compounds are found as impurities in terephthalic acid obtained by liquid phase nitric acid oxidation of para-xylene and other suitable starting materials.

When 2,6-dimethylnaphthalene is the aromatic feed compound for the oxidation reaction and a catalyst comprising cobalt, manganese and bromine components is used, the oxidation reaction mixture directly from the oxidation reactor (also called the total reactor effluent or TRE) contains the reaction solvent, which is typically a mixture of acetic acid and water, the desired 2,6-naphthalene dicarboxylic acid, and impurities including trimellitic acid (TMLA), bromo-2,6-naphthalenedicarboxylic acid (Br-2,6-NDA), 2-formyl-6-naphthoic acid (2-FNA), 2-naphthoic acid (2-NA), a collection of other impurities, and cobalt and manganese catalyst components. The acetic acid and water can be removed by evaporation or distillation from the oxidation reaction mixture to leave a residue of solids. Analysis of these solids provides a useful assessment of all of the solid components in the oxidation reaction mixture and consequently an assessment of the yield of desired product and reaction by-products. In a typical oxidation of 2,6-dimethylnaphthalene, the amount of trimellitic acid in the oxidation reaction mixture solids can be as high as 5 weight percent of the solids and typically about 3-4 weight percent. The amount of 2-formyl-6-naphthoic acid can be as high as 1 weight percent and typically is about 0.4-0.5 weight percent. The amount of bromo-2,6-naphthalene dicarboxylic acids can be as high a 3 weight percent and is typically about 0.2 to 1 weight percent. The total of cobalt and manganese in the solid portion of the oxidation reaction mixture can be as high as 4 weight percent. Although the desired 2,6-naphthalene dicarboxylic acid is generally insoluble in the oxidation reaction mixture, particularly when the oxidation reaction mixture is cooled to a temperature below the oxidation reaction temperature, and can be easily separated from the oxidation reaction mixture, the 2,6-naphthalene dicarboxylic acid recovered is also contaminated with trimellitic acid, 2-formyl-6-naphthoic acid, bromo-2,6-naphthalene dicarboxylic acids, other organic impurities and by-products, as well as the cobalt and manganese oxidation metal catalysts. Furthermore, even when the 2,6-naphthalene dicarboxylic acid is separated from the oxidation reaction mixture at an elevated temperature, and even if the separated 2,6-naphthalenedicarboxylic acid is washed with fresh solvent at an elevated temperature to remove residual mother liquor, the recovered 2,6-naphthalene dicarboxylic acid still contains substantial amounts of the aforementioned impurities by by-products which require removal from the 2,6-naphthalene dicarboxylic acid.

The crude acid produced by the aforesaid liquid-phase oxidation is generally purified by reduction of the impurities therein, for example, by the methods disclosed in the aforesaid U.S. Pat. Nos. 3,584,039; 3,726,915; and 4,405,809. The purification step of the method of the present invention for producing purified aromatic carboxylic acid such as terephthalic acid, isophthalic acid, or naphthalene dicarboxylic acid is conducted at an elevated temperature and pressure in a pressure reaction vessel in the presence of hydrogen gas and a catalyst comprising a carbon carrier containing one or more active hydrogenation components. The crude acid to be purified is dissolved in a purification solvent such as water or a like polar solvent to form a solution containing from about 5 to about 50 weight percent of the crude acid to be purified. Although water is the preferred solvent, other highly suitable polar solvents include the relatively lower molecular weight alkyl carboxylic acids containing from 2 to 6 carbon atoms, typically acetic acid, either alone or admixed with water. When the acid to be purified is terephthalic or isophthalic acid, water is the preferred solvent. When the acid to be purified is a naphthalene dicarboxylic acid, a relatively higher purification temperature is employed and a solvent like acetic acid or a mixture of acetic acid and water containing from about 10 to about 90 weight percent of water is the preferred solvent because of its relatively lower vapor pressure compared to pure or substantially pure water. Suitable reactor temperatures for use in this purification step are in the range of from about 100° C. to about 350° C. Preferably, the temperatures employed in the purification step are in the range of about 225° C. to about 300° C.

The pressure employed in the purification step depends primarily upon the temperature employed therein. Inasmuch as the temperatures at which practical amounts of the crude acid being purified may be dissolved in an aforesaid solvent are substantially above the normal boiling point of the solvent, the process pressures are necessarily considerably above atmospheric pressure to maintain the solution in liquid phase. If the reactor is hydraulically full, the reactor pressure can be controlled by the feed pumping rate. If the reactor has a head space, the reactor pressure can be maintained by gaseous hydrogen alone or in admixture with an inert gas such as water vapor and/or nitrogen in the head space. In general, the reactor pressure during hydrogenation can be in the range of about 200 to about 1,500 pounds per square inch gauge, and usually is in the range of about 900 to about 1,200 pounds per square inch gauge.

In the method of this invention, the solution of crude aromatic carboxylic acid is treated with the hydrogen in a pressure reactor vessel in a first reaction zone containing a hydrogenation catalyst comprising one or more active hydrogenation catalyst components supported on a carbon carrier or support material. The carbon carrier or support is typically in a granular form although pellets or other types of particulate forms of the carrier can be used. When in a granular form, the granules have an average size of about 2 mesh to about 12 mesh (U.S. Sieve Series), more preferably about 4 mesh (4.76 mm) to about 8 mesh (2.38 mm). The carbon carrier is preferably an active carbon, and is most preferably derived from coconut charcoal. Such active carbon typically has a surface area of at least 600 m$^2$/gram (N$_2$; BET Method), preferably about 800 m$^2$/gram to about 1500 m$^2$/gram. While active carbon derived from coconut charcoal in the form of granules is most preferred as a support material for the hydrogenation catalyst component, other porous carboneous supports or substrates can be used, such as those derived from other plant or animal sources.

The hydrogenation catalyst used in the method of this invention contains at least one active hydrogenation component. The most suitable hydrogenation components are the Group VIII metals of the Periodic Table of Elements, including palladium, platinum, rhodium, osmium, ruthenium, and iridium. The hydrogenation catalyst component can be deposited on or added to the carbon carrier material by any standard method known in the art, for example, by treating the carbonaceous carrier with a solution of one or more soluble Group VIII metal compounds such as palladium chloride, and then drying the catalyst to remove excess solvent. The loading of the Group VIII metal on the carbon carrier is suitably in the range of 0.01 weight percent to about 2 weight percent based on the total weight of the finished catalyst, i.e. the total weight being the weight of the dry carbon carrier and the active hydrogenation component. Preferably, the Group VIII metal loading on the carbon carrier is about 0.2 to about 0.8 weight percent. Suitable catalyst and catalyst beds useful in the method of this invention for the purification of aromatic carboxylic acids are described, for example, in U.S. Pat. Nos. 4,394,299; 4,629,715; 4,728,630 and 4,892,972. A suitable palladium-on-carbon catalyst can be obtained, for example, from Engelhard Corporation, Edison, N.J. under the designation "Palladium on Activated Carbon Granules (Carbon Code CG-21)." Also, suitable rhodium-on-carbon catalysts can be obtained from Engelhard Corporation, under the designation "Rhodium on Activated Carbon Granules (Carbon Code CG-21)."

The reactor used in the method of this invention is any reactor vessel that can withstand the temperature and pressure used for the hydrogenation of the solution of impure aromatic carboxylic acid. The preferred reactor configuration is a cylindrical reactor positioned vertically and having the hydrogenation catalyst contained therein in a fixed bed. In the preferred mode of operation, the solution of impure aromatic carboxylic acid is added to the reactor vessel at a position at or near the top portion of the reactor vessel and the solution of impure aromatic carboxylic acid flows down through the bed of hydrogenation catalyst contained in the reactor vessel in the presence of hydrogen gas wherein impurities in the solution are reacted with the hydrogen gas. In this preferred mode, a product stream containing purified aromatic carboxylic acid is removed from the reactor vessel at a position at or near the bottom of the reactor.

In a conventional reactor vessel apparatus for purifying aromatic carboxylic acids, the hydrogenation catalyst comprising the carbon carrier and active hydrogenation catalyst component is held within the reactor vessel by a screen or other means that retains the catalyst particles in the reactor, yet allows the relatively free passage of the solution of aromatic carboxylic acid in the purification solvent. The means used for retaining the catalyst particles can be a flat mesh screen or a screen made by closely spaced parallel wires. Other suitable catalyst retaining means include, for example, a tubular Johnson screen or a perforated plate. The means used for retaining the catalyst particles must be constructed of a material that is suitably resistant to corrosion and it must also be of an appropriate strength to efficiently retain the catalyst bed. Most suitably, the means used for retaining the catalyst bed has openings of 1 mm or less and is constructed of a metal such as stainless steel, titanium or Hastelloy C. However, when such a screen or other means used for retaining the hydrogenation catalyst is employed, the relatively soft carbon catalyst particles are forced against the screen or other retaining means and the carbon particles undergo abrasion or attrition. Additionally, the large volume of liquid reaction mixture passing through the relatively small openings of the screen is the cause of turbulence that aggravates the attrition of the carbon particles. The abrasion causes the formation of fine carbon particles that pass through the screen or other retaining means and contaminate the purified aromatic carboxylic acid recovered from the reaction mixture. However, the formation of such fine carbon particulates is reduced or eliminated by the method of this invention wherein a layer of abrasion resistant material is positioned directly adjacent to the screen or other retaining means. Therefore, rather than having the soft catalyst pressing against the screen, the abrasion resistant material presses against the screen thereby eliminating the abrasion of the carbon particles caused by the catalyst retaining means. The layer of abrasion resistant material also functions as a trap for carbon particles from the catalyst bed. Thus, in the method of this invention, the mixture of crude aromatic carboxylic acid passes through a first bed of catalyst comprising a carbon carrier having a hydrogenation catalyst component, then through a second bed of abrasion resistant material, wherein the abrasion resistant material is positioned directly against the screen or other means used for retaining the hydrogenation catalyst in the reactor vessel.

The abrasion resistant material used in the method of this invention must allow for the passage of the reaction mixture comprising aromatic carboxylic acid and purification solvent. The abrasion resistant material can be granular in shape; preferably, however, it is in a regular shape such as a pellet, extrudate, sphere, tablet and like divided form. A spherical form is highly preferred because it does not have easily eroded or abraded edges. In contrast, the carbon carrier for the hydrogenation catalyst is typically irregular in shape with corners that are susceptible to breakage. The abrasion resistant material must be more abrasion resistant than the carbon carrier used for the hydrogenation catalyst of this invention. Preferably, the abrasion resistance should be such that the material does not form particulates that break off under the reaction conditions employed and pass through the screen or other means used for retaining the catalyst bed in the reactor vessel. The abrasion resistant materials used in the method of this invention suitably have a crush strength of at least 15 lbs., more preferably a crush strength of at least 30 lbs., and most preferably a crush strength of at least 100 lbs., as measured by ASTM D4179-82, "Standard Test Method for Single Pellet Crush Strength of Formed Catalyst Shapes." The abrasion resistant materials useful in this invention have a "Loss on attrition" of less than 3%, more preferably less than 2%, and most preferably less than 1%, as measured by ASTM D4058-81, "Standard Test Method for Attrition and Abrasion of Catalysts and Catalyst Carriers." Additionally, it is preferable that the abrasion resistant material be inert under the reaction conditions used in the method of this invention. Materials such as gamma alumina or silica which slowly disintegrate in the reaction mixture are not as preferable as other materials that are substantially more inert. Abrasion resistant materials suitable for the method of this invention include, for example, titanium dioxide, alpha alumina, zirconium dioxide, niobium oxide and silicon carbide. Other abrasion resistant materials include titanium and stainless steel, suitably used in a porous, sintered form. However, these metallic materials can also be used in the method of this invention in other divided forms such as rings, small spheres, coils, turnings or other shapes and configurations. Alpha alumina, particularly in the form of spheres is a preferred abrasion resistant material useful in this invention. Because the abrasion resistant materials used in the method of this invention do not need to have a high surface area, as is typically necessary for catalyst support materials, the abrasion resistant inorganic materials can be calcined at high temperatures in order to maximize their strength and abrasion resistance.

The reactor employed in the purification method of this invention can be operated in several modes. For example, a predetermined liquid level can be maintained in the reactor and hydrogen can be fed in, for any given reactor pressure, at a rate sufficient to maintain the predetermined liquid level. The difference between the actual reactor pressure and the vapor pressure of the crude acid solution present is the hydrogen partial pressure in the reactor vapor space. Alternatively, if hydrogen is fed in admixture with an inert gas such as nitrogen, the difference between the actual reactor pressure and the vapor pressure of the crude acid solution present is the combined partial pressure of hydrogen and the inert gas admixed therewith. In this case the hydrogen partial pressure can be calculated from the known relative amounts of hydrogen and inert gas present in the admixture. In yet another operating mode, the reactor can be filled with the solution of aromatic acid so as to provide no reactor vapor space. That is, the reactor can be operated as a hydraulically full system with dissolved hydrogen being fed to the reactor by flow control. In such an instance, the solution hydrogen concentration can be modulated by adjusting the hydrogen flow rate to the reactor. If desired, a pseudohydrogen partial pressure value can be calculated from the solution hydrogen concentration which, in turn, can be correlated with the hydrogen flow rate to the reactor.

In the operating mode where process control is effected by adjusting the hydrogen partial pressure, the hydrogen partial pressure in the reactor preferably is in the range of about 10 pounds per square inch gauge to about 200 pounds per square inch gauge, or higher, depending upon the service pressure rating of the reactor, the degree of contamination of the aforesaid crude acid, the activity and age of the particular catalyst employed, and like processing considerations. In the operating mode where process control is effected by adjusting directly the hydrogen concentration in the feed solution, the latter usually is less than saturated with respect to hydrogen and the reactor itself is hydraulically full. Thus, an adjustment of the hydrogen flow rate to the reactor will result in the desired control of hydrogen concentration in the solution. In general, the amount of hydrogen to be supplied to the purification reactor under reaction conditions is, of course, sufficient to effect the desired hydrogenation.

The space velocity reported as weight of the crude aromatic acid solution per weight of catalyst per hour in the purification step is from about 1 hour$^{-1}$ to about 25 hours$^{-1}$, preferably from about 2 hours$^{-1}$ to about 15 hours$^{-1}$. The residence time of the solution in the catalyst bed varies, depending upon the space velocity.

A preferred abrasion resistant material used in the method of this invention is titanium dioxide. The titanium dioxide can be formed by an extrusion technique in any convenient form that can be used in a packed bed. In one embodiment, at least about one weight percent, preferably at least about 90 weight percent, and more preferably 100 weight percent of the titanium dioxide support is in the rutile crystal phase. In another embodiment, the titanium dioxide is formed by calcination of titanium dioxide at a temperature in the range of from about 600° C., preferably from about 800° C., and more preferably from about 900° C., to about 1200° C., preferably to about 1100° C., and more preferably to about 1000° C. In this embodiment, preferably at least 5 weight percent, more preferably at least 70 weight percent, and most preferably substantially 100 weight percent, of the titanium dioxide which is calcined is initially in the anatase crystal phase. In addition, the titanium dioxide being calcined contains preferably from about 0.05, more preferably from about 0.2, and most preferably from about 0.5 weight percent, preferably to about 5, and more preferably to about 3 weight percent of a sulfur-containing component, calculated as elemental sulfur. In yet another embodiment, the titanium dioxide contains less than 500 parts per million by weight, preferably less than 100 parts per million by weight, of a sulfur-containing component, calculated as elemental sulfur.

In a further embodiment, the titanium dioxide has a total specific surface area of preferably less than about 40 square meters per gram, more preferably less than about 20 square meters per gram, and most preferably less than about 10 square meters per gram. In another embodiment, the titanium dioxide has an average pore diameter of at least about 10 nanometers (nm), preferably at least about 20 nm. In another embodiment, at least one weight percent of the titanium dioxide support is in the rutile crystal phase whose support contains less than 500 parts per million by weight of a sulfur-containing component, calculated as elemental sulfur, has a total specific surface area of less than about 40 square meters per gram, has an average pore diameter of at least about 10 nm, and is formed by calcination at a temperature of from about 600° C. to about 1200° C. of titanium dioxide of which at least 50 weight percent is in the anatase crystal phase and contains at least one weight percent of a sulfur-containing component, calculated as elemental sulfur. In the method of this invention, the depth of the layer of abrasion resistant material in the reactor vessel is such that it will substantially and more preferably completely prevent the contact of the catalyst with the screen or other retaining means. The ratio of the depth of the hydrogenation catalyst bed to the bed of inert material can be about 1000:1 to about 0.1:1, preferably about 100:1 to about 1:1, and most preferably about 30:1 to about 2:1. The depth of the bed of abrasion resistant material is preferably about 1 cm to about 100 cm, preferably about 10 cm to about 50 cm. In the method of this invention, the abrasion resistant material can also contain one or more active hydrogenation components such as the Group VIII metals discussed hereinabove. When a tubular screen design is used, it is placed within a bed of the abrasion resistant material so that all of the surfaces of the screen are adjacent to the abrasion resistant material.

After hydrogenation, the treated solution of aromatic acid from the reactor is cooled to a temperature—for example, about 150° C. or below—that is sufficiently low for crystallization of the purified acid to occur but sufficiently high that the impurities and their reduction products remain dissolved in the resulting mother liquor. Thereafter the mother liquor containing the dissolved impurities and their reduction products is separated from the crystallized purified acid, whereby purified crystals of fiber and thin film grade acid are recovered.

This invention is also a layered catalyst bed suitable for purifying aromatic carboxylic acids in a feedstream comprising an aromatic carboxylic acid dissolved in a purification solvent, comprising: a first bed of hydrogenation catalyst comprising a carbon carrier material and at least one hydrogenation catalyst component; and a second bed down stream from the first bed comprising at least one abrasion resistant material. A mesh screen can be used to separate the first and second bed.

DETAILED DESCRIPTION OF THE DRAWING

A mode of operating the method of this invention is shown in FIG. 1. A mixture of purification solvent (such as water) and crude aromatic carboxylic acid (such as terephthalic acid) is added to pressure purification reactor 10 through inlet 20. Hydrogen gas is added to reactor 10 through gas inlet 30. The solution of terephthalic acid in water flows down and through catalyst bed 40. Catalyst bed 40 contains active carbon having deposited thereon 0.5 weight percent palladium. After passing through the catalyst bed 40 the reaction mixture passes through bed 50 of abrasion resistant material such as titanium dioxide in extruded form or alpha alumina in spherical form. Retaining screen 60 retains the bed of titanium dioxide and bed of catalyst within the reactor. By using the reactor shown in FIG. 1, having the first bed of catalyst and second bed of abrasion resistant material, the relatively soft, easily abraded carbon carrier material of the hydrogenation catalyst does not press against the retaining screen which otherwise causes the attrition of the carbon carrier into small particles that can easily pass through the screen and contaminate the purified terephthalic acid.

The present invention will be more clearly understood from the following specific examples.

EXAMPLES

EXAMPLE 1

A pilot plant reactor of the down flow type and equipped with a fixed catalyst bed one inch in diameter and 6.5 inches in length is used. The end portion reactor is fitted with a 20 mesh screen for retaining the catalyst bed in the reactor. The hydrogenation catalyst in the fixed bed is constituted by a particulate commercial palladium-on-carbon catalyst. Between the hydrogenation catalyst bed and the screen is positioned a 1 inch bed of titanium dioxide extrudates. The pilot plant reactor is operated at a temperature of about 280° C. (535° F.) and at a hydrogen partial pressure of 100 psig. The total reactor pressure during operation is 1025 psig. Crude terephthalic slurry containing about 12 weight percent terephthalic acid and about 2,700 ppm by weight of 4-carboxybenzaldehyde is fed to the reactor at a rate of 1.6 kg of slurry per hour. The effluent from the reactor is cooled to ambient temperature to crystalize purified terephthalic acid. The purified terephthalic is examined using a microscope and is found to contain low levels of carbon particulates.

EXAMPLE 2 (COMPARATIVE)

The procedure of Example 1 is repeated except that the bed of titanium dioxide is not added to the reactor and the particulate palladium-on-carbon catalyst is positioned directly against the catalyst retaining screen. The resulting purified terephthalic acid contains a greater level of carbon particulates from the hydrogen catalyst component in comparison to the purified terephthalic acid of Example 1.

From the above description, it is apparent that, while only certain embodiments and various modifications will be apparent from the above description to those skilled in the art, these alternatives are considered equivalents and within the spirit and scope of the present invention.

Having described the invention, what is claimed is:

1. A method for purifying an aromatic carboxylic acid comprising passing a mixture of purification solvent and aromatic carboxylic acid, at a temperature of about 100° C. to about 350° C. and at a pressure sufficient to maintain the purification solvent substantially in the liquid phase through a first zone in a reactor vessel in the presence of hydrogen gas, the first zone having a catalyst comprising a carbon carrier material and at least one hydrogenation catalyst component, and subsequently passing the mixture through a second zone comprising abrasion-resistant material, the second zone being positioned within the reactor vessel so that it is directly adjacent to a means for retaining catalyst within the reactor vessel.

2. The method of claim 1 wherein the aromatic carboxylic acid is selected from the group consisting of terephthalic acid, 2,6-naphthalenedicarboxylic acid and isophthalic acid.

3. The method of claim 2 wherein the aromatic carboxylic acid is prepared by the liquid phase, heavy metal catalyzed oxidation of benzene or naphthalene having oxidizable alkyl or acyl ring substituents.

4. The method of claim 1 wherein the hydrogenation catalyst component comprises at least one Group VIII metal of the Periodic Table of Elements.

5. The method of claim 4 wherein the loading of the Group VIII metal component is about 0.01 to about 2 weight percent.

6. The method of claim 1 wherein the abrasion resistant material has a loss on attrition of less than 4%.

7. The method of claim 1 wherein the abrasion resistant material is selected from the group consisting of titanium dioxide, alpha alumina, zirconium dioxide, niobium oxide, silicon carbide, titanium and stainless steel.

8. The method of claim 1 wherein the abrasion resistant material has a regular shape.

9. The method of claim 1 wherein the abrasion resistant material is titanium dioxide in the shape of extrudates.

10. The method of claim 1 wherein the abrasion resistant material is alpha alumina.

11. The method of claim 10 wherein the alpha alumina is in the form of spheres.

* * * * *